(12) United States Patent
Levin, II et al.

(10) Patent No.: US 8,386,416 B2
(45) Date of Patent: Feb. 26, 2013

(54) DATABASE RATING INDEX

(75) Inventors: Shawn M. Levin, II, Philadelphia, PA (US); Aviad Adlersberg, Royersford, PA (US)

(73) Assignee: Accenture Global Services Limited, Dublin (IE)

( * ) Notice: Subject to any disclaimer, the term of this patent is extended or adjusted under 35 U.S.C. 154(b) by 597 days.

(21) Appl. No.: 12/607,569

(22) Filed: Oct. 28, 2009

(65) Prior Publication Data

US 2011/0099141 A1 Apr. 28, 2011

(51) Int. Cl.
G06F 15/00 (2006.01)
G06F 15/18 (2006.01)
(52) U.S. Cl. .......................................................... 706/62
(58) Field of Classification Search .................... 706/62
See application file for complete search history.

(56) References Cited

U.S. PATENT DOCUMENTS 6,631,365 B1 * 10/2003 Neal et al. ..................... 707/690
2010/0185464 A1 * 7/2010 Houriet et al. .................... 705/3

OTHER PUBLICATIONS

G. Hoffmann and M. Malek, "Meeting Deadlines in Complex Systems: A Probabilistic Approach", Inst. fur Informatik, May 2004, pp. 1-21.*

* cited by examiner

*Primary Examiner* — Kakali Chaki
*Assistant Examiner* — Vincent Gonzales
(74) *Attorney, Agent, or Firm* — Fish & Richardson P.C.

(57) ABSTRACT

Methods, computer-readable media, and apparatuses for determining the status of a clinical database in order to characterize the quality of the database. The status may be based on the proportion of outstanding items in relation to relative milestones. A database rating index for a database is determined from risk factors, where the database rating index is indicative of a status of the clinical database and may be determined from risk factors, where each risk factor includes an issue parameter and a subject parameter, the issue parameter equals the number of occurrences for the corresponding issue, and the subject parameter corresponds to the number of patients associated with the issue parameter. The database rating index may be determined from one of a set of functions that depend on an issue health score and a subject health score.

17 Claims, 8 Drawing Sheets

DATABASE RATING INDEX

BACKGROUND

Clinical trials are often conducted to allow safety and efficacy data to be collected for new drugs or devices. Clinical trials can take place once satisfactory information has been gathered on the quality of the product and its non-clinical safety, and approval is granted in the country where the trial is taking place. Depending on the type of product and the stage of its development, investigators enroll healthy volunteers and/or patients into small pilot studies initially, followed by larger scale studies in patients that often compare the new product with the currently prescribed treatment. As positive safety and efficacy data are gathered, the number of patients is typically increased. Clinical trials may vary in size from a single center in one country to multicenter trials in multiple countries. Although a sizable cost for a full series of clinical trials may be incurred, the burden of paying for all the necessary people and services is typically borne by the sponsor who may be a governmental organization, a pharmaceutical, or biotechnology company. Since the diversity of roles may exceed resources of the sponsor, often a clinical trial is managed by an outsourced partner such as a contract research organization.

Clinical trials involving new drugs are commonly classified into four phases with pharmaceutical studies. However, pre-clinical studies are often conducted in order to obtain preliminary efficacy, toxicity, and pharmacokinetic information before the clinical trials themselves. Pre-clinical studies assist pharmaceutical companies to decide whether a drug candidate has scientific merit for further development as an investigational new drug.

Phase I trials is the first stage of testing in human subjects. A small (20-50) group of healthy volunteers is typically selected. This phase includes trials designed to assess the safety (pharmacovigilance), tolerability, pharmacokinetics, and pharmacodynamics of a drug. These trials are often conducted in an inpatient clinic, where the subject can be observed by full-time staff.

Once the initial safety of the study drug has been confirmed in Phase I trials, Phase II trials are performed on larger groups (20-300) and are designed to assess how well the drug works, as well as to continue Phase I safety assessments in a larger group of volunteers and patients. When the development process for a new drug fails, this usually occurs during Phase II trials when the drug is discovered not to work as planned or to have toxic effects.

Phase III studies are randomized controlled multicenter trials on large patient groups (300-3,000 or more depending upon the disease/medical condition studied) and are aimed at being the definitive assessment of how effective the drug is in comparison with current gold standard treatment. Because of the size and comparatively long duration, Phase III trials are typically the most expensive, time-consuming and difficult trials to design and run, especially in therapies for chronic medical conditions. It is common practice that certain Phase III trials will continue while the regulatory submission is pending at the appropriate regulatory agency. This allows patients to continue to receive possibly lifesaving drugs until the drug can be obtained by purchase. Once a drug has proved satisfactory after Phase III trials, the trial results are usually combined into a large document containing a comprehensive description of the methods and results of human and animal studies, manufacturing procedures, formulation details, and shelf life. This collection of information makes up the regulatory submission that is provided for review to the appropriate regulatory authorities in different countries. Regulatory authorities review the submission to determine whether to give the sponsor approval to market the drug. Most drugs undergoing Phase III clinical trials in the United States may be marketed under Federal Drug Administration (FDA) norms with proper recommendations and guidelines, but in case of any adverse effects being reported anywhere, the drugs may be recalled immediately from the market. While most pharmaceutical companies refrain from this practice, many drugs undergo Phase III clinical trials in the market.

Phase IV trial is also known as the post marketing surveillance trial. Phase IV trials involve the safety surveillance (pharmacovigilance) and ongoing technical support of a drug after it receives permission to be sold. Phase IV studies may be required by regulatory authorities or may be undertaken by the sponsoring company for competitive (finding a new market for the drug) or other reasons (e.g., the drug may not have been tested for interactions with other drugs, or on certain population groups such as pregnant women, who are unlikely to subject themselves to trials). The safety surveillance is designed to detect any rare or long-term adverse effects over a much larger patient population and longer time period than was possible during the Phase I-III clinical trials.

Each phase of the drug approval process is typically treated as a separate clinical trial. The drug-development process normally proceeds through all four phases over many years. If the drug successfully passes through Phases I, II, and III, the drug will usually be approved by the national regulatory authority for use in the general population. Phase IV involves post-approval studies. A clinical trial typically takes a number of years to complete. For example, about eight years passes from the time a cancer drug enters clinical trials until it receives approval from regulatory agencies for sale to the public. Drugs for other diseases often have similar timelines. Consequently, avoiding delays in collecting data during the clinical trial may reduce development costs while providing beneficial drugs to the public in a more expeditious manner.

BRIEF SUMMARY

Aspects of the invention provide methods, apparatuses, and computer-readable media for determining the status of a clinical database in order to characterize the quality of the database. The status may be based on the proportion of outstanding items in relation to relative milestones.

With another aspect of the invention, a database rating index (DRI) for a clinical database is determined from risk factors, where the database rating index is indicative of a status of the clinical database. The probability of locking the clinical database by a desired date may then be predicted from the database rating index. The database rating index may be determined from risk factors, where risk factor includes an issue parameter and a subject parameter, the issue parameter equals the number of occurrences for the corresponding issue, and the subject parameter corresponds to the number of patients associated with the issue parameter. Exemplary risk factors include missing pages, outstanding queries, unlocked patients, and missing site data verification (SDV).

With another aspect of the invention, the database rating index is determined from one of a set of functions that depend on an issue health score, a subject health score, and a number of days until locking the clinical database.

BRIEF DESCRIPTION OF THE DRAWINGS

Aspects of the invention are illustrated by way of example and not limited in the accompanying figures in which like reference numerals indicate similar elements and in which.

DETAILED DESCRIPTION

Embodiments support determining the status of a clinical database (e.g., associated with pharmaceutical research) in order to characterize the quality of the database. The status may be based on the proportion of outstanding items in relation to relative milestones. Different milestones may be assessed, including a scheduled lock date for the database and an interim analysis. The status of different phases of the database may be analyzed including database start up, maintenance, and finalization. Database start up is the process in which a database is built for data collection. This includes creating the collection devices (forms) as well as programming data validations in relation to the protocol. Maintenance is the active phase of study where data collection is ongoing. Finalization is the close of the active phase where all subjects have completed the study, in which all of the entered data entered is locked and finalized to prevent further modification and is delivered for clinical analysis.

Figure 1:
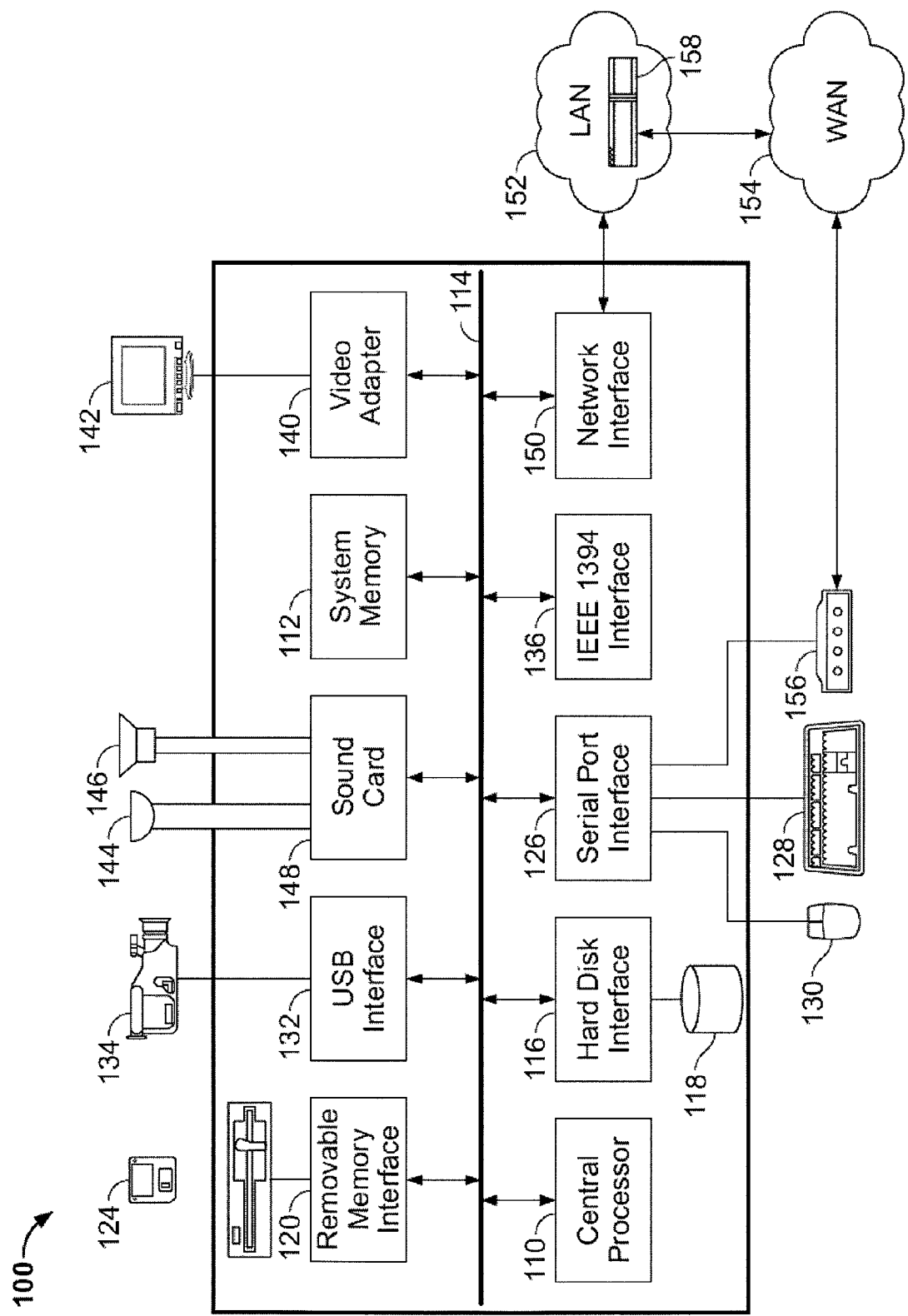
FIG. 1 shows a computer system used in a system for determining a status of a database in accordance with an embodiment of the invention.
Figure 2:
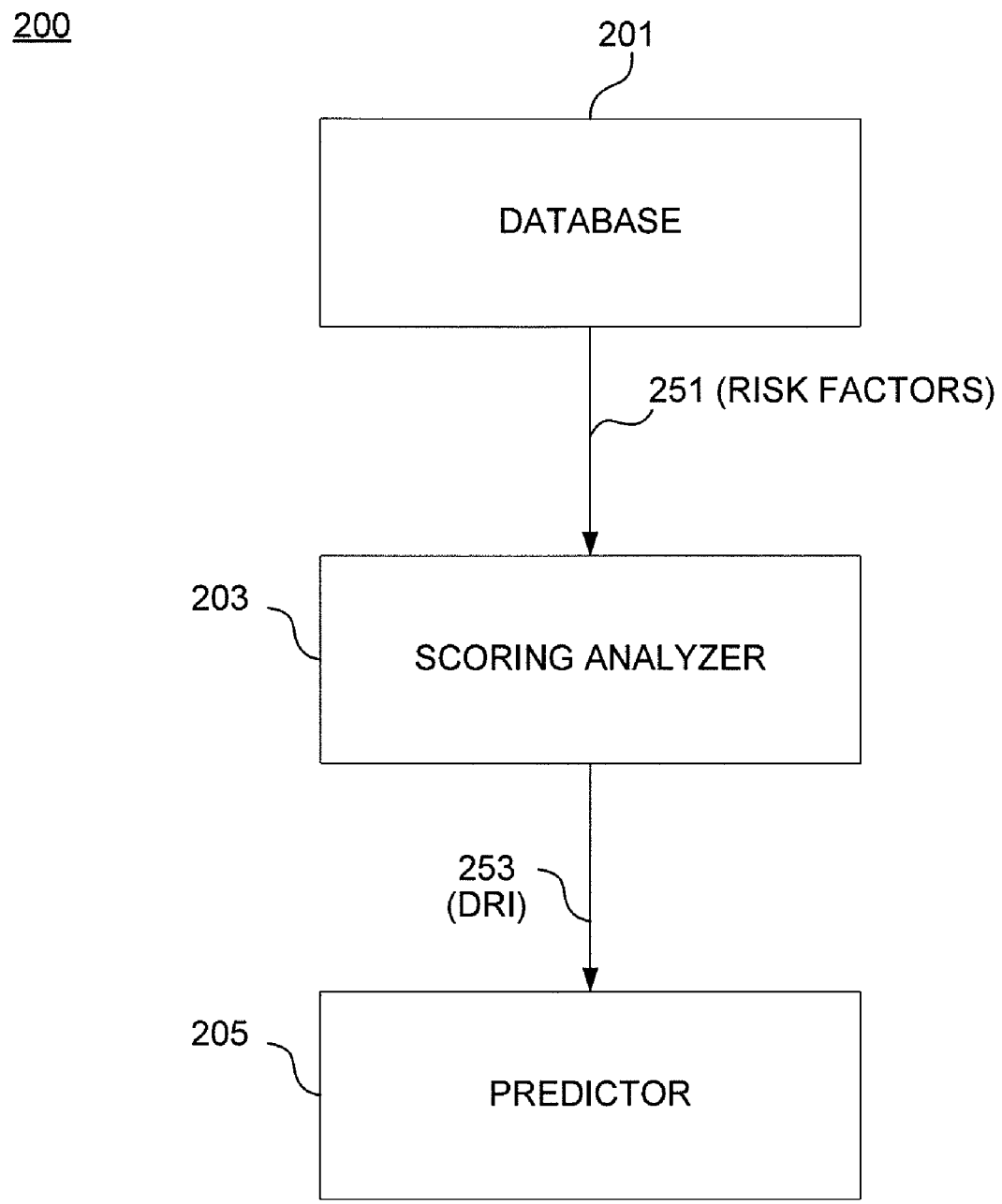
FIG. 2 shows a process for determining a database rating of clinical database and for predicting the locking of the database at a targeted date in accordance with an embodiment of the invention.
Figure 3:
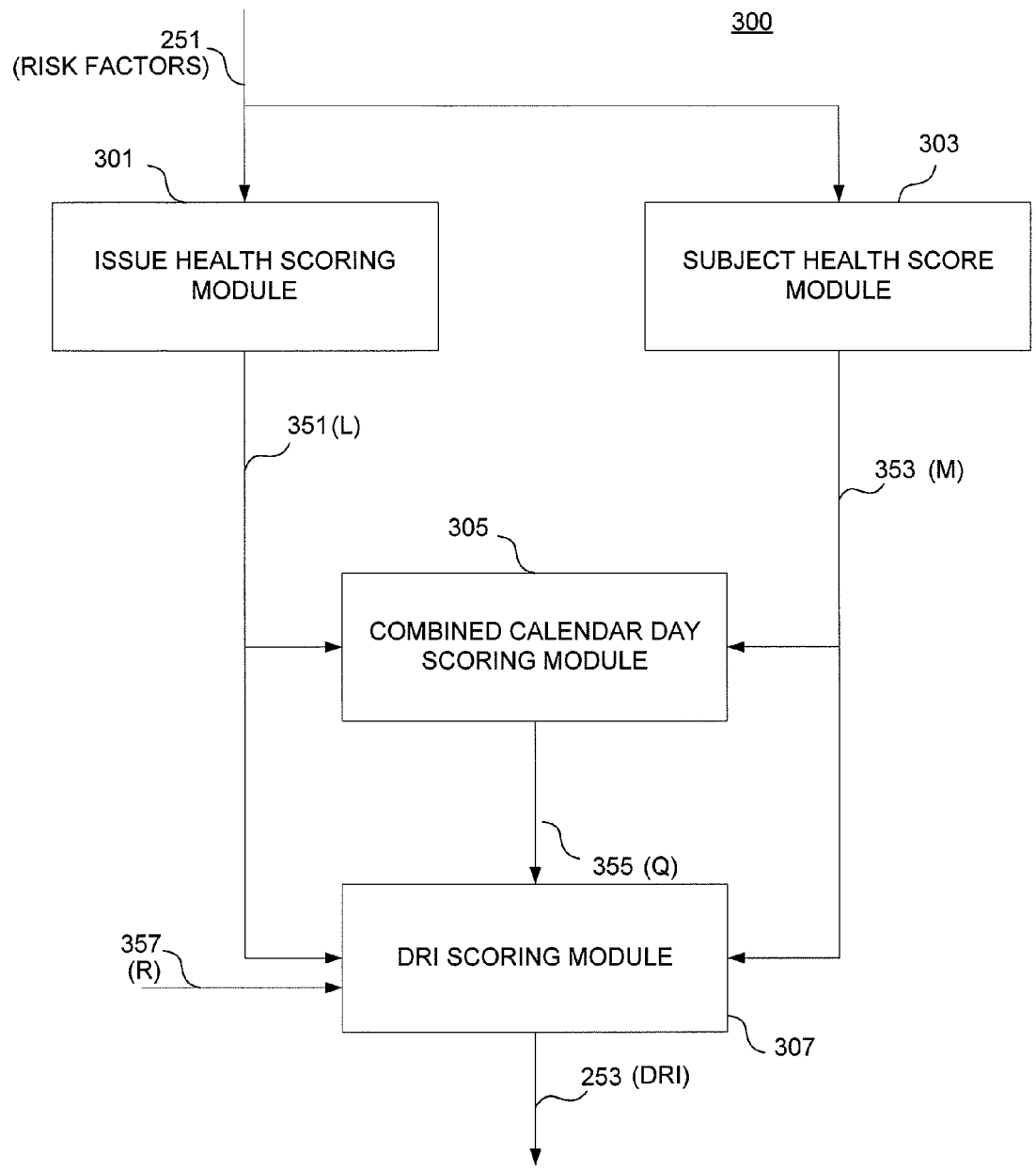
FIG. 3 shows a process for determining a database rating index for a clinical database from risk factors in accordance with an embodiment of the invention.
Figure 4:
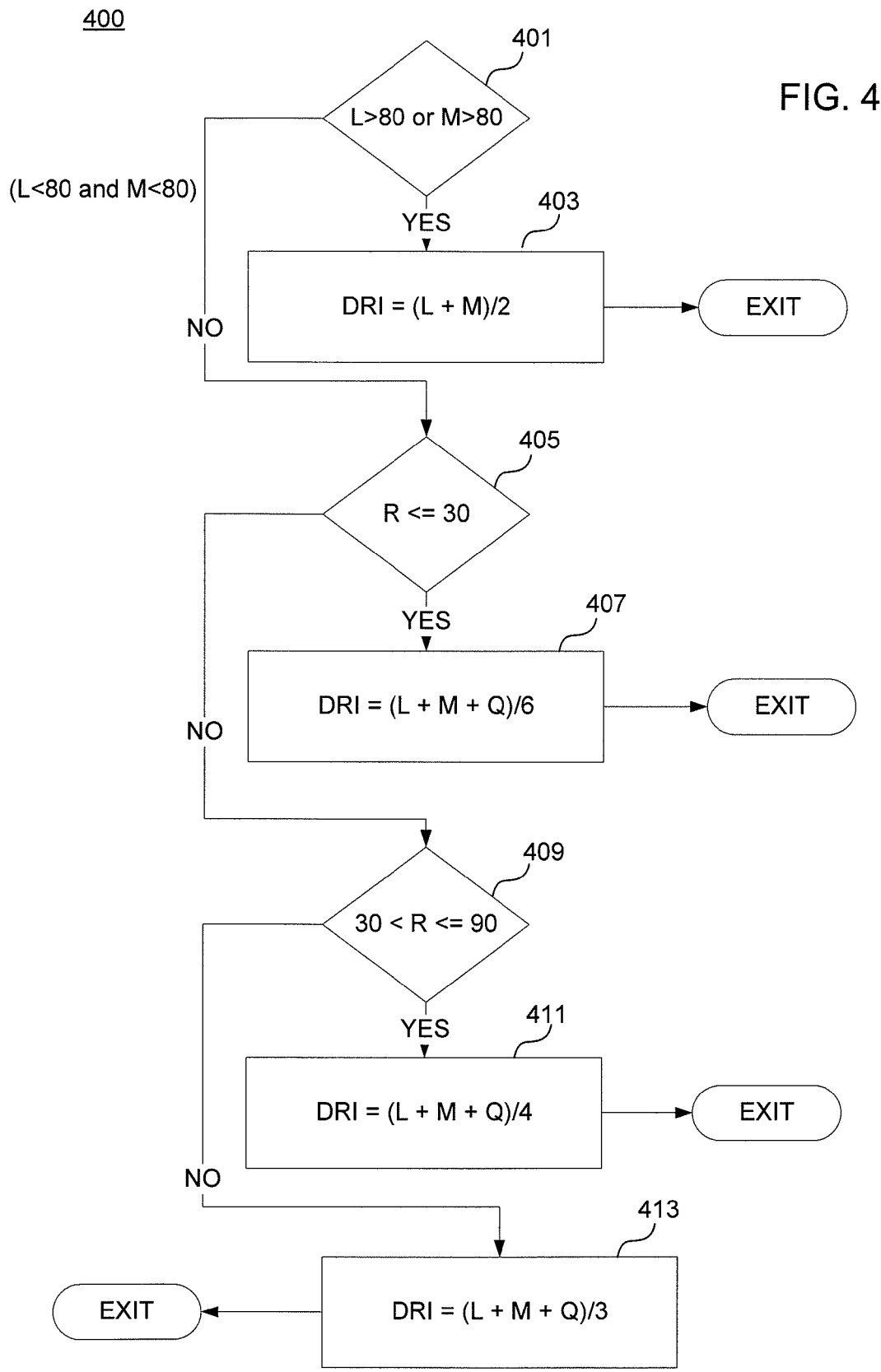
FIG. 4 shows a flow diagram for determining a database rating index from an issue health score, subject health score, and calendar day information in accordance with an embodiment of the invention.

Elements of the present invention may be implemented with computer systems, such as the system 100 shown in FIG. 1. System 100 may execute processes (e.g., processes 200, 300, and 400 as shown in FIGS. 2, 3, and 4, respectively) to the status of a clinical database in accordance with aspects for the invention as disclosed herein.

Computer 100 includes a central processor 110, a system memory 112 and a system bus 114 that couples various system components including the system memory 112 to the central processor unit 110. System bus 114 may be any of several types of bus structures including a memory bus or memory controller, a peripheral bus, and a local bus using any of a variety of bus architectures. The structure of system memory 112 is well known to those skilled in the art and may include a basic input/output system (BIOS) stored in a read only memory (ROM) and one or more program modules such as operating systems, application programs and program data stored in random access memory (RAM).

Computer 100 may also include a variety of interface units and drives for reading and writing data. In particular, computer 100 includes a hard disk interface 116 and a removable memory interface 120 respectively coupling a hard disk drive 118 and a removable memory drive 122 to system bus 114. Examples of removable memory drives include magnetic disk drives and optical disk drives. The drives and their associated computer-readable media, such as a floppy disk 124 provide nonvolatile storage of computer readable instructions, data structures, program modules and other data for computer 100. A single hard disk drive 118 and a single removable memory drive 122 are shown for illustration purposes only and with the understanding that computer 100 may include several of such drives. Furthermore, computer 100 may include drives for interfacing with other types of computer readable media. A storage device (e.g., hard disk drive 118) may store predetermined values that are accessed when processing a process (e.g., process 300) when executing program data.

A user can interact with computer 100 with a variety of input devices. FIG. 1 shows a serial port interface 126 coupling a keyboard 128 and a pointing device 130 to system bus 114. Pointing device 128 may be implemented with a mouse, track ball, pen device, or similar device. Of course one or more other input devices (not shown) such as a joystick, game pad, satellite dish, scanner, touch sensitive screen or the like may be connected to computer 100.

Computer 100 may include additional interfaces for connecting devices to system bus 114. FIG. 1 shows a universal serial bus (USB) interface 132 coupling a video or digital camera 134 to system bus 114. An IEEE 1394 interface 136 may be used to couple additional devices to computer 100. Furthermore, interface 136 may configured to operate with particular manufacture interfaces such as FireWire developed by Apple Computer and i.Link developed by Sony. Input devices may also be coupled to system bus 114 through a parallel port, a game port, a PCI board or any other interface used to couple and input device to a computer.

Computer 100 also includes a video adapter 140 coupling a display device 142 to system bus 114. Display device 142 may include a cathode ray tube (CRT), liquid crystal display (LCD), field emission display (FED), plasma display or any other device that produces an image that is viewable by the user. Additional output devices, such as a printing device (not shown), may be connected to computer 100.

Sound can be recorded and reproduced with a microphone 144 and a speaker 166. A sound card 148 may be used to couple microphone 144 and speaker 146 to system bus 114. One skilled in the art will appreciate that the device connections shown in FIG. 1 are for illustration purposes only and that several of the peripheral devices could be coupled to system bus 114 via alternative interfaces. For example, video camera 134 could be connected to IEEE 1394 interface 136 and pointing device 130 could be connected to USB interface 132.

Computer 100 can operate in a networked environment using logical connections to one or more remote computers or other devices, such as a server, a router, a network personal computer, a peer device or other common network node, a wireless telephone or wireless personal digital assistant. Computer 100 includes a network interface 150 that couples system bus 114 to a local area network (LAN) 152. Networking environments are commonplace in offices, enterprise-wide computer networks and home computer systems.

A wide area network (WAN) 154, such as the Internet, can also be accessed by computer 100. FIG. 1 shows a modem unit 156 connected to serial port interface 126 and to WAN 154. Modem unit 156 may be located within or external to computer 100 and may be any type of conventional modem such as a cable modem or a satellite modem. LAN 152 may also be used to connect to WAN 154. FIG. 1 shows a router 158 that may connect LAN 152 to WAN 154 in a conventional manner.

It will be appreciated that the network connections shown are exemplary and other ways of establishing a communications link between the computers can be used. The existence of any of various well-known protocols, such as TCP/IP, Frame Relay, Ethernet, FTP, HTTP and the like, is presumed, and computer 100 can be operated in a client-server configuration to permit a user to retrieve web pages from a web-based server. Furthermore, any of various conventional web browsers can be used to display and manipulate data on web pages.

The operation of computer 100 can be controlled by a variety of different program modules. Examples of program modules are routines, programs, objects, components, data structures, etc., that perform particular tasks or implement particular abstract data types. The present invention may also be practiced with other computer system configurations, including hand-held devices, multiprocessor systems, microprocessor-based or programmable consumer electronics, network PCS, minicomputers, mainframe computers, personal digital assistants and the like. Furthermore, the invention may also be practiced in distributed computing environments where tasks are performed by remote processing devices that are linked through a communications network. In a distributed computing environment, program modules may be located in both local and remote memory storage devices.

FIG. 2 shows process 200 for determining a database rating index 253 of clinical database 201 and for predicting the locking of database 201 at a targeted date in accordance with an embodiment of the invention. Multiple and often consistently changing variables may directly affect the timing of database finalization With traditional systems it is often difficult to quantify risks (currently assessed qualitatively), and consequently it is difficult to compare different databases to one another on a consistent basis. Moreover, tools are typically not available to be able to predict the behavior of database finalization with traditional systems.

With an aspect of the disclosure, a standardized variable combines and quantifies the major risks into one value in order to characterize the quality of database relative to finalization With some embodiments, the standardized variable comprises database rating index (DRI) 253. DRI 253 may be customized per client based on each unique risk and relative milestone that is associated with client's database. With an exemplary embodiment for a clinical database, scoring analyzer 203 utilizes risk factors 251 including missing pages, outstanding queries, unlocked patients, and missing site data verification (SDV) as well as calendar days until milestone to determine DRI 253. Each risk variable is weighted appropriately based on sequence of events and relative risk in terms of meeting milestones. Exemplary risk factors include:

Missing Pages—expected pages that have not been received

Outstanding Queries—questions sent to the site, but have not yet been answered

Unlocked Patients—a subject where data that has not been finalized and is still subject to data entry and modification Missing SDV—Source data verification is performed by the Site Monitor to compare the source data from the site to the database to ensure its accuracy. These are subjects that still have this check pending.

As will be further discussed, DRI 253 is a metric that considers: the number of actual issues (raw values), the number of issues relative to subjects, and the number of calendar days until milestone (which may be weighted using a parabolic curve function). With some embodiments, DRI 253 is constrained to a value between 0-100 (where the higher the value, the more stable database 201 is) and the value of DRI 253 should be 100 in order to lock database 201. To facilitate interpretation by a user, an indication of DRI 253 may be displayed as a trichotomous color scale, where DRI 253 is shown in red, yellow, or green when the value is between 0-50, 50-80, and 80-100, respectively.

Predictor 205 may utilize DRI 253 to predict a probability of locking database 201 according to the targeted date. For example, database 201 may be typically locked when the collected data is sufficiently stable so that the collected data can be properly evaluated by a governmental agency, e.g., the Food and Drug Administration (FDA). Once a client-specific formula is obtained for determining DRI 253, the formula may be used to analyze historical data. Calculate DRI 253 may be calculated on finalized studies from multiple time slices to analyze DRI 253 based on statistical measures (e.g., $\chi$ and $\sigma$). With an exemplary embodiment using custom reports, DRIs for other finalized studies may be calculated for the last 120 days before locking database 201. With a sufficiently large set of DRI data, a normal curve for DRIs may be established so that DRI 253 (i.e., database rating index for the current study) may be compared to the normal curve. Consequently, a z-score (which is a standard score that indicates how many standard deviations the current study is above or below the mean) may be obtained to compare the status of the current study with previous studies. Predictor 205 may compare current studies to view quantitative trends of potential issues that may jeopardize the scheduled lock date. Predictor 205 may further determine confidence intervals for each study and their relative milestones.

FIG. 3 shows process 300 for determining database rating index 253 for clinical database 201 from risk factors 251 in accordance with an embodiment of the invention.

Weight factors for each risk factor is determine so that the relative importance may be assigned when determining DRI 253. With some embodiments, the sum of all the weight factors equal 1. The highest weight for any one risk factor is determined by the total number of risk factors (x). The lowest risk factor (LR) equals $(1/x^2)$. The weight factor is increased by 2*LR for the next important risk factor. For example, if three risk factors are identified (high risk, medium risk, and low risk) and are associated with $W_{high}$, $W_{medium}$, and $W_{low}$, respectively, then the above algorithm results in the weight factor $W_{10}=(1/3^2)=0.11$. The weight factor for each subsequent risk is increased by 0.11*2=0.22. Consequently, $W_{low}=0.11$, $W_{medium}=0.33$, and $W_{high}=0.56$ (where $W_{low}+W_{medium}+W_{high}=0.11+0.33+0.56=1$).

With another exemplary embodiment, there are four risk factors: missing pages (highest risk), outstanding queries, missing SDV, and unlocked patients (lowest risk). Weight factors $W_1$ (corresponding to the lowest risk), $W_2$, $W_3$, and $W_4$ (corresponding to the highest risk) is set to 0.1, 0.2, 0.3, and 0.4 (i.e., the above algorithm is not used). In order to determine DRI 253, module 301 determines issue_health_score (L) 351 and module 303 determines subject_health_score (M) 353.

Each risk factor (e.g., missing pages, outstanding queries, unlocked patients, and missing site data verification (SDV)) comprises an issue parameter and a subject parameter. The issue parameter equals the number of occurrences for the corresponding issue and the subject parameter equals number of patients associated with the corresponding issue.

Module 301 processes the issue parameters for risk factors 251 to obtain issue_health_score (L) 351 by calculating:

$$\text{issue\_health\_score} = (0.1(a)+0.2(b)+0.3(c)+0.4(d)+e)/(a+b+c+d+e)*100 \quad \text{(EQ. 1)}$$

where a=number of missing pages, b=number of outstanding queries, c=number of missing SDV, d=number of unlocked patients, and e=total number of patients. The weight factors are reversed for the issue parameters because there is an inverse relationship with the highest risk factor versus the final score. The higher the missing pages are in the exemplary embodiment, the lower the value of the issue health score and thus the bigger reduction this score receives in the numerator. EQ. 1 calculates a score based on the raw number of issues Module 303 processes the subject parameters for risk factors 251 to obtain subject health score (M) 353 by calculating:

$$\text{subject health score} = (1-((0.4(f)+0.3(g)+0.2(h)+0.1(i))/(j)))*100 \quad \text{(EQ. 2)}$$

where f=number of patients missing pages, g=number of patients associated with outstanding queries, h=number of patients associated with missing SDV, i=number of unlocked patients, and j=total number of patients in the study. The subject matter score compares the number of patients with a certain issue to the total number of patients. Thus, the bigger the number of missing pages, for example, the lower the score. This effect is counteracted by subtracting the resulting ration from 1 before multiplying by 100.

Module 305 determines combined calendar day score (Q) 355 from a calendar_factor and a calendar_function. With some embodiments, K is equal to the number of calendar days until milestone (i.e., today's date–ock date). The calendar_factor is defined by:

$$\text{calendar\_factor} = 1/\text{square root}(K) \quad \text{(EQ. 3)}$$

The calendar factor in EQ. 3 is characterized by an inverse parabolic curve.

The calendar function produces a value between 0-100 which factors in the calendar factor with the individual risk scores. The calendar function is determined both for data_by_issue_risks and for data_by_subject_risks by the following:

$$\text{calendar\_function\_for\_data\_by\_issue\_risks} = L-(L*K) \quad \text{(EQ. 4)}$$

$$\text{calendar\_function\_for\_data\_by\_subject\_risks} = M-(M*K) \quad \text{(EQ. 5)}$$

where L=issue_health_score, M=subject health score, and K=calendar_factor as discussed above.

Combined_calendar_day_score (Q) 355 is equal to an average of the calendar_function_for_Data_by_Issue_Risks (CFI) and the calendar_function_for_data_by_subject risks (CFS) as follows:

$$\text{combined\_calendar\_day\_score} = (CFI+CFR)/2 \quad \text{(EQ. 6)}$$

Module 307 then determines DRI 253 from issue_health_score (L) 351 subject_health_score 353, combined_calendar_day_score (Q) 355, and the number of calendar days until milestone (R). DRI 253 considers issue_health_score 351 and subject_health_score 353 relative to combined_calendar_day_score 355.

With some embodiments, DRI 253 is determined by a set of functions in order to reflect the risks as shown by flow diagram 400 in FIG. 4. When either issue_health_score 351 or subject health score 353 is over 80, the calendar function is not factored into the final score because the number of days until milestone typically ceases to be a risk factor under those circumstances. If both scores 351 and 353 are under 80, the calendar function is added since under those circumstances the number of days until the milestone typically becomes a risk factor that should be included. DIR 253 is further weighted if the number of days until milestone is less than 90 days and again if they are less than 30 days since risks may increase dramatically at those time points for studies.

Process 400 determines database rating index 253 from issue_health_score 351, subject_health_score 353, and calendar day information in accordance with an embodiment of the invention. A series of formulas used to calculate the overall status (a number between 1 and 100) that characterizes the quality of a clinical database (pharmaceutical research) considering the proportion of outstanding items in relation to relative milestones. Separate formulas may be used for database start up, maintenance, and finalization. For example, flow diagram 400 is typically executed for different times before locking so that DRI 253 is determined as a function of time and is exemplified in FIG. 7.

The exemplary embodiment shown in flow diagram 400 incorporates the following set of logic:

If L or M>80 Then $$DRI=(L+M)/2 \quad \text{(EQ. 7)}$$

Else
If R<=30 and >0 and L or M<80 Then $$DRI=(L+M+Q)/6 \quad \text{(EQ. 8)}$$

If R>30 And <=90 And L or M<80 Then $$DRI=(L+M+Q)/4 \quad \text{(EQ. 9)}$$

If R>90 L or M<80 Then $$DRI=(L+M+Q)/3 \quad \text{(EQ. 10)}$$

where L=issue_health_score, M=subject health score, R=number of calendar_days_before_milestone, and Q=combined_calendar_day_score as discussed above.

If block 401 determines that the issue_health_score (L) or the subject_health_score (M) is greater than 80, then block 403 is executed in accordance with EQ. 7. Otherwise, process 400 processes blocks 407, 411, and 415 based on the number of calendar days before milestone (R). If block 405 determines that R is less than or equal to 30 days, then block 407 is executed in accordance with EQ. 7. If block 409 determines that R is greater than 30 and less than or equal to 90, then block 411 is executed in accordance with EQ. 9. Otherwise R is greater than 90, so block 413 is executed in accordance with EQ. 10.

Figure 5:
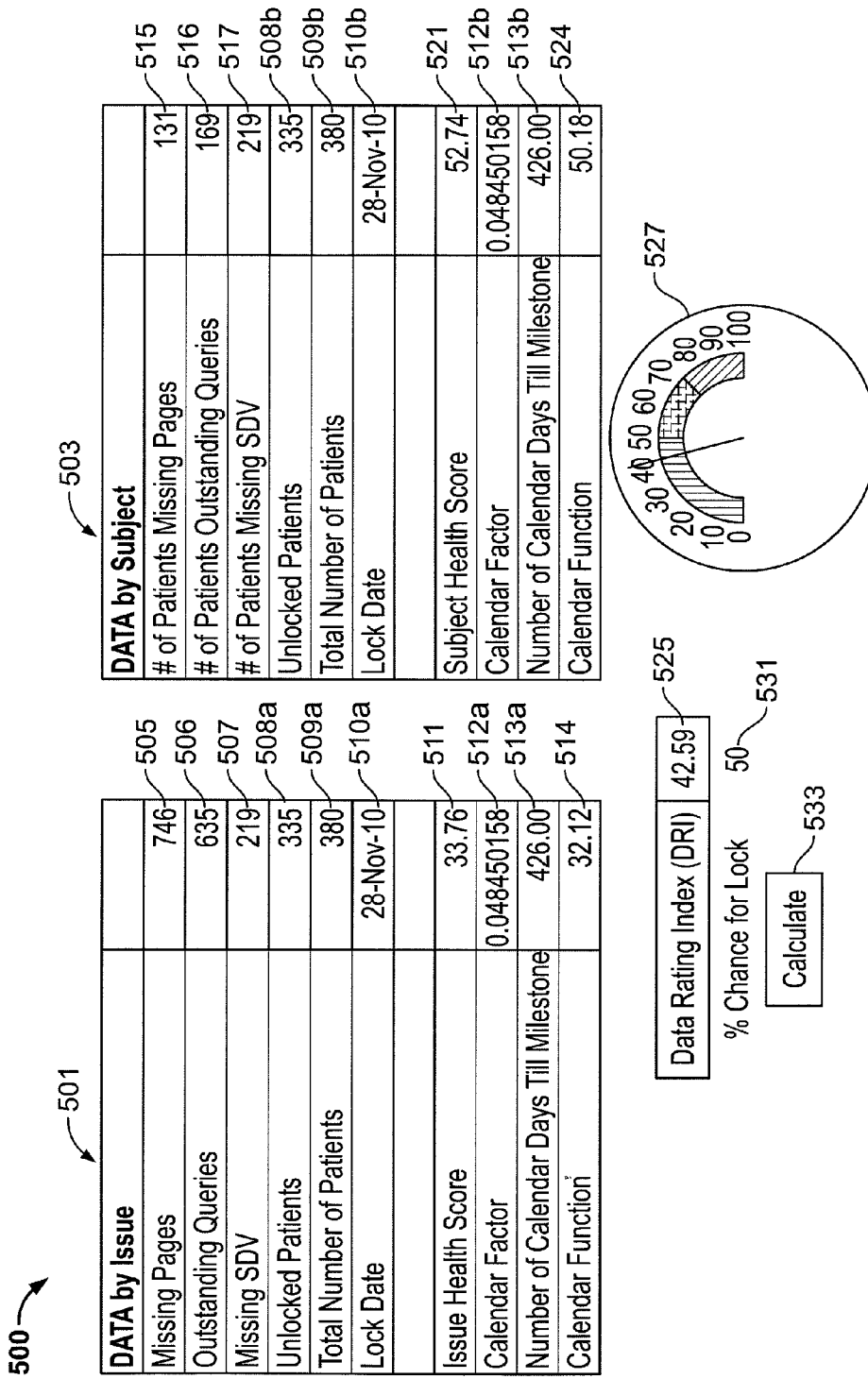
FIG. 5 shows a first exemplary screenshot for calculating a database rating index for a clinical database, determining a probability of locking the clinical database, providing a course of action for locking the clinical database, and updating historical tables in accordance with an embodiment of the invention.

FIG. 5 shows exemplary screenshot 500 for calculating a database rating index for a clinical database, determining a probability of locking the clinical database, and providing a course of action for locking the clinical database, and updating historical tables in accordance with an embodiment of the invention. Issue parameters 505-508a, corresponding subject parameters 515-517 and 508b, total number of patients 509a,b, and the scheduled lock date 510a,b are entered into the corresponding data fields. The unlocked patients 508a,b, number of total patients 509a,b, scheduled lock date 510a,b, calendar factor 512a,b, and number of calendar days until milestone 513a,b are the same for both data by issue 501 and data by subject 503.

Issue_health_score 511, subject_health_score 521, calendar function 514, and calendar function 524 are determined from EQ. 1, EQ. 2, EQ. 4, and EQ. 5, respectively, as discussed above. DRI 525 is subsequently determined from one of the set of equations EQ. 7-EQ. 10 in response to a user request through entry 533. While DRI 525 is displayed (with a value of 42.59 as shown), the DRI is also shown in as simulated gauge 527, where a DRI value between 0-50, 50-80, and 80-100 is displayed in red, yellow, and green, respectively.

From DRI 525 and historical data for similar databases, system 100 determines the probability for locking clinical database 201 and displays the prediction as displayed output 531 (with a value of 50% as shown). The probability may be determined in various manners. For example, the DRI may be sampled at different times before the scheduled lock date and compared with similar historical or hypothetical data. The comparison may be based on statistical approaches, e.g., a chi-square test. For example, by comparing DRI 525 to the normal curve of data from previous studies, we can obtain a z-score may be determined as discussed previously. The z-score can be used to calculate the percentile of the current study to all other studies. Consequently, a probability may be calculated from the number of times a previous study with a similar DRI completed on schedule.

Figure 6:
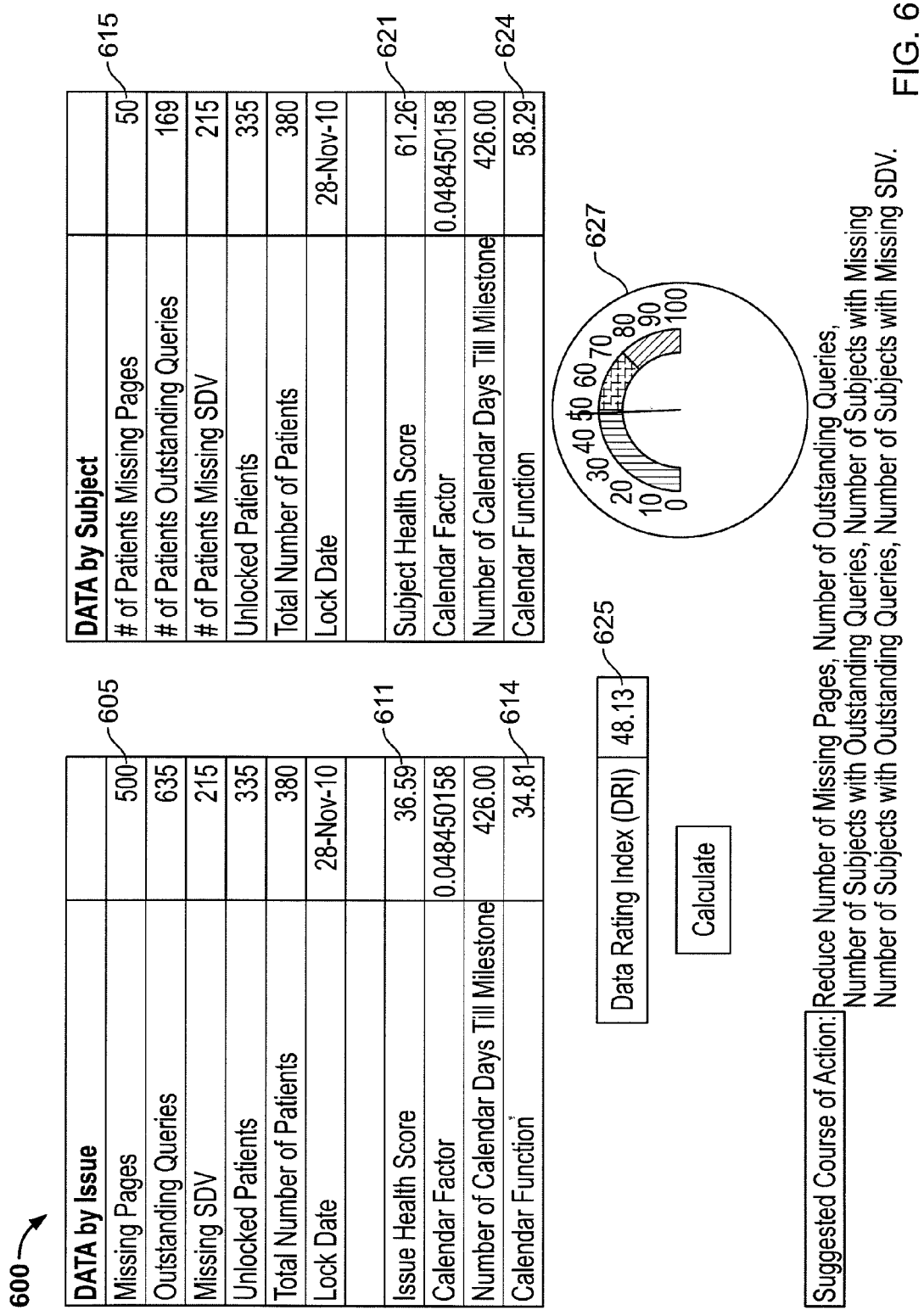
FIG. 6 shows a second exemplary screenshot for calculating a database rating index for a clinical database, determining a probability of locking the clinical database, providing a course of action for locking the clinical database, and updating historical tables in accordance with an embodiment of the invention.

System 100 may also suggest a course of action for improving the DRI as shown as displayed field 529. For example, the number of missing pages and the number of subjects with missing pages may be reduced to improve the DRI. FIG. 6 shows a second exemplary screenshot for calculating a database rating index in which this course of action is achieved. Comparing entries 505 and 605 (missing pages) and 515 and 615 (number of patients with missing pages), one observes that the number of missing pages is reduced from 746 to 500 pages and the number of patients is reduced from 131 to 50 patients. Consequently, the DRI is increased from 42.59 to 48.13 (shown as displayed output 625) by reducing the number of missing pages and corresponding subjects.

Figure 7:
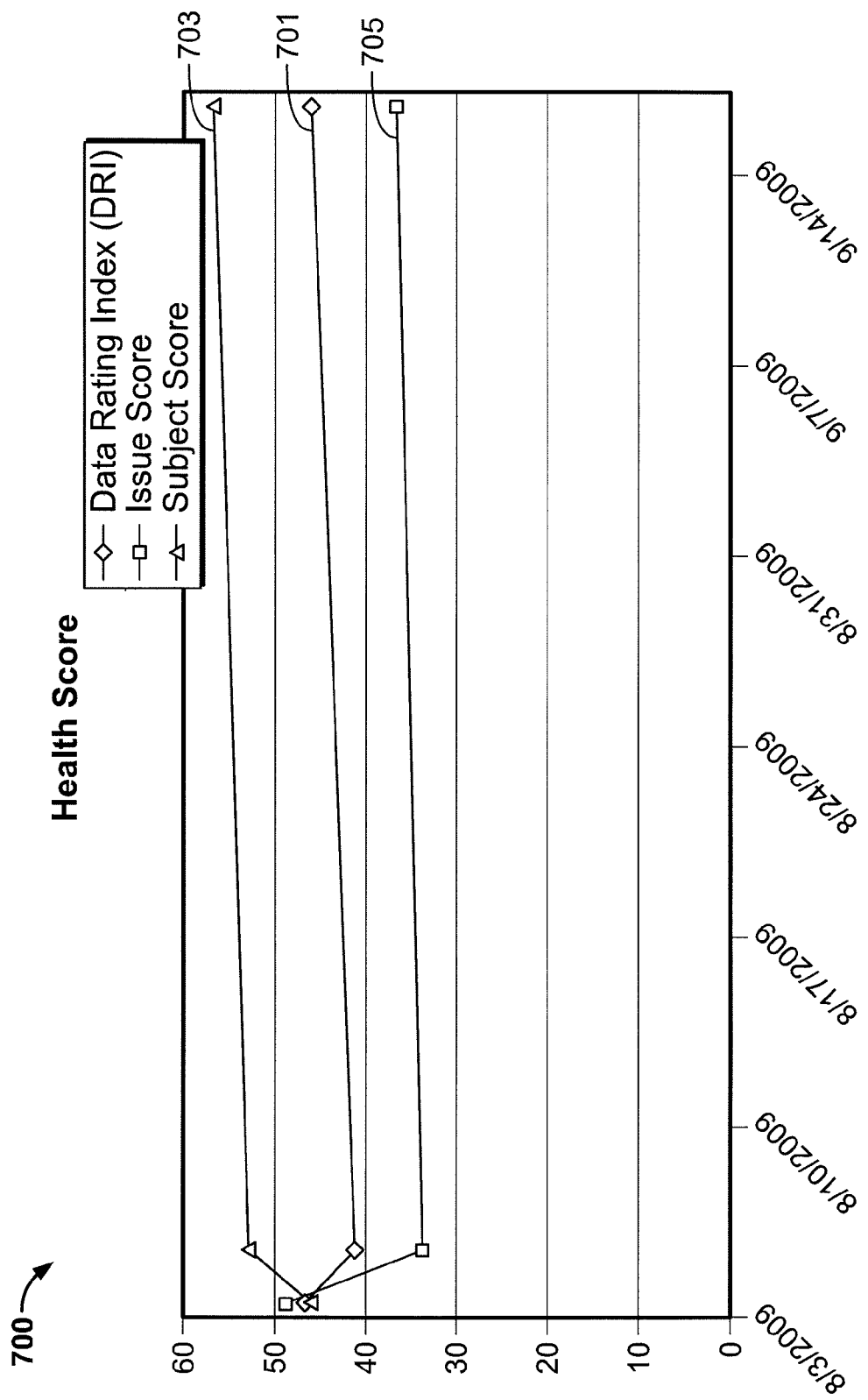
FIG. 7 shows an exemplary screenshot of a historical graph for the health score in accordance with an embodiment of the invention.

FIG. 7 shows exemplary screenshot 700 of a historical graph for the health score in accordance with an embodiment of the invention. Curves 701, 703, and 705 show the DRI, subject_health_score, and issue_health_score, respectively, as function of time (in which database 201 is sampled on Aug. 3, Aug. 5, and Sep. 28, 2009). Curves 701, 703, and 705 are completed by connecting lines between the sampled points.

Figure 8:
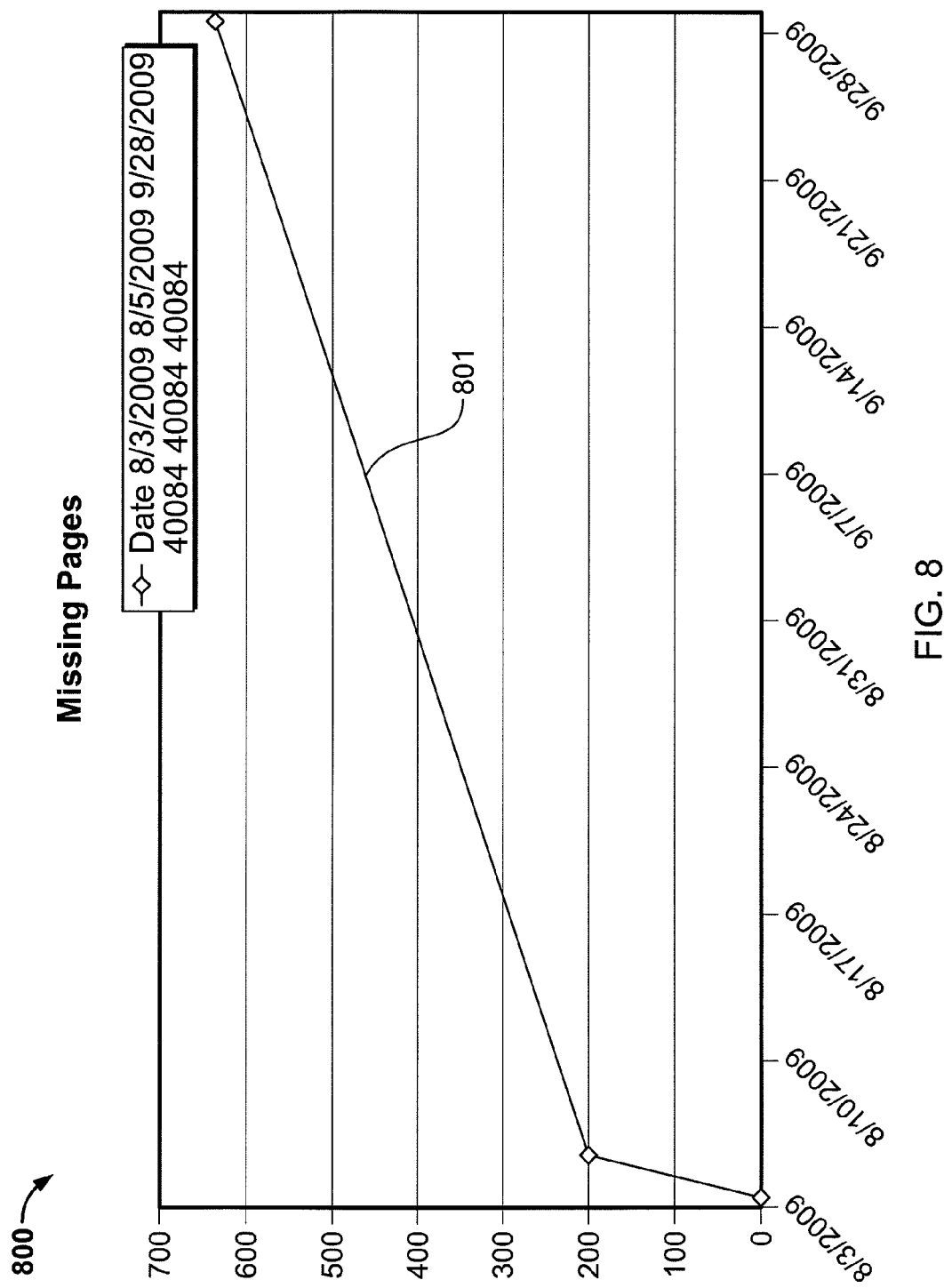
FIG. 8 shows an exemplary screenshot of a historical graph for missing pages in accordance with an embodiment of the invention.

FIG. 8 shows exemplary screenshot 800 of a historical graph for missing pages in accordance with an embodiment of the invention. The number of missing pages is shown as a function of time as curve 801. Typically, as a study is ongoing and more subjects are entered into a clinical trial, the number of missing pages will first rise before decreasing. Curve 801 demonstrates the phase of a study where missing pages increase.

As can be appreciated by one skilled in the art, a computer system with an associated computer-readable medium containing instructions for controlling the computer system may be utilized to implement the exemplary embodiments that are disclosed herein. The computer system may include at least one computer such as a microprocessor, a cluster of microprocessors, a mainframe, and networked workstations.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

We claim:

1. A computer-assisted method comprising:
   determining, by a computer, a database rating index (DRI) for a clinical database from a plurality of risk factors, the database rating index being indicative of a status of the clinical database, determining the database rating index further comprising:
   determining a calendar factor from a desired date and a current date;
   determining a calendar score from an issue health score, a subject health score, and the calendar factor; and
   determining the database rating index from the issue health score, the subject health score, and the calendar score; and
   predicting, by the computer, a probability of locking the clinical database by the desired date from the database rating index.

2. The method of claim 1, further comprising:
   generating a recommendation for improving the database rating index.

3. The method of claim 1, wherein a first risk factor comprises a first issue parameter and a first subject parameter and a second risk factor comprises a second issue parameter and a second subject parameter and wherein the first issue parameter corresponds to a number of occurrences of a first issue, the first subject parameter corresponds to a number of patients associated with the first issue parameter, the second issue parameter corresponds to a number of occurrences of a second issue, and the second subject parameter corresponds to a number of patients associated with the second issue parameter, the method further comprising:
   determining the issue health score from the first issue parameter and the second issue parameter; and
   determining the subject health score from the first subject parameter and the second subject parameter.

4. The method of claim 1, further comprising:
   determining the database rating index from a plurality of functions that depend on the issue health score, the subject health score, and the calendar score; and
   selecting one of the plurality of functions based on a number of days until a milestone date.

5. The method of claim 1, wherein the database rating index corresponds to a start up of the clinical database.

6. The method of claim 1, wherein the database rating index corresponds to maintenance of the clinical database.

7. The method of claim 1, wherein the database rating index corresponds to a finalization of the clinical database.

8. The method of claim 1, further comprising:
   determining the database rating index for a plurality of time slices for the clinical database; and
   comparing the data rating index with historical data; and
   obtaining a trend of the clinical database from the comparing.

9. An apparatus comprising:
   a memory; and
   a processor configured to retrieve instructions from the memory and to perform:
   determining, by a computer, a database rating index (DRI) for a clinical database from a plurality of risk factors, the database rating index being indicative of a status of the clinical database, determining the database rating index further comprising:
   determining a calendar factor from the a desired date and a current date;
   determining a calendar score from an issue health score, a subject health score, and the calendar factor; and determining the database rating index from the issue health score, the subject health score, and the calendar score; and generating a recommendation for improving the database rating index.

10. The apparatus of claim 9, wherein the processor is further configured to:

predict a probability of locking the clinical database by a desired date from the database rating index.

11. The apparatus of claim 9, wherein the first issue parameter corresponds to a number of occurrences of a first issue, the first subject parameter corresponds to a number of patients associated with the first issue parameter, the second issue parameter corresponds to a number of occurrences of a second issue, and the second subject parameter corresponds to a number of patients associated with the second issue parameter and wherein the processor is further configured to:

determine the issue health score from the first issue parameter and the second issue parameter; and determine the subject health score from the first subject parameter and the second subject parameter, wherein the first subject parameter corresponds to a first number of patients associated with the first issue parameter and wherein the first subject parameter corresponds to a first number of patients associated with the first issue parameter.

12. The apparatus of claim 9, wherein the processor is further configured to:

determine the database rating index from a plurality of functions that depend on the issue health score, the subject health score, and the calendar score; and select one of the plurality of functions based on a number of days until a milestone date.

13. The apparatus of claim 9, wherein the processor is further configured to:

determine the database rating index for a plurality of time slices for the clinical database;

compare the data rating index with historical data; and obtain a trend of the clinical database from the comparing.

14. A non-transitory computer-readable storage medium storing computer-executable instructions that, when executed, cause a processor to perform a method comprising:

determining, by a computer, a database rating index (DRI) for a clinical database from a plurality of risk factors, the database rating index being indicative of a status of the clinical database, determining the database rating index further comprising:

determining a calendar factor from a desired date and a current date;

determining a calendar score from an issue health score, a subject health score, and the calendar factor; and further determining the database rating index from the issue health score, the subject health score, and the calendar score;

predicting, by the computer, a probability of locking the clinical database by the desired date from the database rating index; and generating a recommendation for improving the database rating index.

15. The computer-readable medium of claim 14, wherein the method further comprises:

determining the issue health score from the first issue parameter and the second issue parameter; and determining the subject health score from the first subject parameter and the second subject parameter, wherein the first issue parameter corresponds to a number of occurrences of a first issue, the first subject parameter corresponds to a number of patients associated with the first issue parameter, the second issue parameter corresponds to a number of occurrences of a second issue, and the second subject parameter corresponds to a number of patients associated with the second issue parameter.

16. The computer-readable medium of claim 14, wherein the method further comprises:

determining the database rating index from a plurality of functions that depend on the issue health score, the subject health score, and the calendar score; and selecting one of the plurality of functions based on a number of days until a milestone date.

17. The computer-readable medium of claim 14, wherein the method further comprises:

determining the database rating index for a plurality of time slices for the clinical database; and comparing the data rating index with historical data; and obtaining a trend of the clinical database from the comparing.

* * * * *

UNITED STATES PATENT AND TRADEMARK OFFICE
CERTIFICATE OF CORRECTION

PATENT NO. : 8,386,416 B2
APPLICATION NO. : 12/607569
DATED : February 26, 2013
INVENTOR(S) : Shawn M. Levin and Aviad Adlersberg Page 1 of 1

It is certified that error appears in the above-identified patent and that said Letters Patent is hereby corrected as shown below:

In the Claims:

Column 10, Line 63 at Claim 9; replace:
"determining a calendar factor from the a desired date" with
-- determining a calendar factor from a desired date --

Signed and Sealed this
Twenty-fourth Day of December, 2013

Margaret A. Focarino
*Commissioner for Patents of the United States Patent and Trademark Office*